(12) United States Patent
Petruno et al.

(10) Patent No.: US 10,753,931 B2
(45) Date of Patent: *Aug. 25, 2020

(54) ASSAY TEST STRIPS WITH MULTIPLE LABELS AND READING SAME

(75) Inventors: Patrick T. Petruno, San Jose, CA (US); John F. Petrilla, Palo Alto, CA (US); Michael J. Brosnan, Fremont, CA (US); Rong Zhou, Sunnyvale, CA (US); Daniel B. Roitman, Menlo Park, CA (US)

(73) Assignee: ALVERIX, INC., Franklin Lakes, NJ (US)

( * ) Notice: Subject to any disclaimer, the term of this patent is extended or adjusted under 35 U.S.C. 154(b) by 1096 days.

This patent is subject to a terminal disclaimer.

(21) Appl. No.: 12/410,182

(22) Filed: Mar. 24, 2009

(65) Prior Publication Data

US 2009/0180929 A1 Jul. 16, 2009

Related U.S. Application Data

(60) Division of application No. 11/236,152, filed on Sep. 26, 2005, now Pat. No. 7,521,259, which is a continuation-in-part of application No. 11/112,807, filed on Apr. 22, 2005, now Pat. No. 8,128,871.

(51) Int. Cl.
| | |
|---|---|
| *G01N 33/558* | (2006.01) |
| *G01N 33/58* | (2006.01) |
| *G01N 21/77* | (2006.01) |
| *G01N 35/00* | (2006.01) |

(52) U.S. Cl.
CPC ......... *G01N 33/558* (2013.01); *G01N 33/582* (2013.01); *G01N 2021/7786* (2013.01); *G01N 2035/00108* (2013.01)

(58) Field of Classification Search
USPC ................................ 977/700, 773, 788, 918
See application file for complete search history.

(56) References Cited

U.S. PATENT DOCUMENTS

| | | | | |
|---|---|---|---|---|
| 4,849,338 | A | * 7/1989 | Litman et al. | ............... 435/7.91 |
| 4,902,278 | A | 2/1990 | Maget et al. | |
| 4,916,056 | A | * 4/1990 | Brown et al. | ................ 435/7.92 |
| 4,960,691 | A | 10/1990 | Gordon et al. | |
| 5,030,558 | A | * 7/1991 | Litman et al. | ............... 435/7.91 |
| 5,132,097 | A | 7/1992 | Van Deusen et al. | |
| 5,217,832 | A | 6/1993 | Joslin et al. | |
| 5,281,395 | A | 1/1994 | Markart et al. | |

(Continued)

FOREIGN PATENT DOCUMENTS

| | | |
|---|---|---|
| CA | 2210559 | 12/2001 |
| JP | H09297832 A | 11/1997 |

(Continued)

*Primary Examiner* — Christopher L Chin
(74) *Attorney, Agent, or Firm* — Knobbe, Martens, Olson & Bear LLP

(57) ABSTRACT

In one aspect, an assay test strip includes a test label that specifically binds a target analyte and a control label that is free of any specific binding affinity for the target analyte and has a different optical characteristic than the test label. In another aspect, an assay test strip includes a test label that specifically binds a target analyte and at least one non-specific-binding label that is free of any specific binding affinity for the target analyte. Systems and methods of reading assay test strips also are described.

10 Claims, 7 Drawing Sheets

(56) References Cited

U.S. PATENT DOCUMENTS

| | | | |
|---|---|---|---|
| 5,304,813 A | 4/1994 | De Man | |
| 5,371,687 A | 12/1994 | Holmes, II et al. | |
| 5,424,220 A | 6/1995 | Goerlach-Graw et al. | |
| 5,442,169 A | 8/1995 | Kunz | |
| 5,514,602 A * | 5/1996 | Brooks et al. | 436/525 |
| 5,519,210 A | 5/1996 | Berner et al. | |
| 5,550,362 A | 8/1996 | Sherman | |
| 5,559,041 A | 9/1996 | Kang et al. | |
| 5,580,794 A | 12/1996 | Allen | |
| 5,602,040 A | 2/1997 | May et al. | |
| 5,837,546 A | 11/1998 | Allen et al. | |
| 5,856,203 A | 1/1999 | Robinson et al. | |
| 5,861,256 A | 1/1999 | Glass et al. | |
| 5,961,451 A | 10/1999 | Reber et al. | |
| 6,017,767 A * | 1/2000 | Chandler | 436/514 |
| 6,136,610 A | 10/2000 | Polito et al. | |
| 6,180,409 B1 | 1/2001 | Howard et al. | |
| 6,217,744 B1 | 4/2001 | Crosby | |
| 6,235,241 B1 | 5/2001 | Catt et al. | |
| 6,267,722 B1 | 7/2001 | Anderson et al. | |
| 6,268,162 B1 | 7/2001 | Phillips et al. | |
| 6,274,323 B1 | 8/2001 | Bruchez et al. | |
| 6,281,785 B1 | 8/2001 | Hamaguchi | |
| 6,300,141 B1 | 10/2001 | Segal et al. | |
| 6,326,144 B1 * | 12/2001 | Bawendi et al. | 435/6 |
| 6,377,894 B1 | 4/2002 | Deweese et al. | |
| 6,379,622 B1 * | 4/2002 | Polak et al. | 422/82.06 |
| 6,394,952 B1 | 5/2002 | Anderson et al. | |
| 6,403,037 B1 | 6/2002 | Chang et al. | |
| 6,483,582 B2 | 11/2002 | Modlin et al. | |
| 6,561,643 B1 | 5/2003 | Walker et al. | |
| 6,585,341 B1 | 7/2003 | Walker et al. | |
| 6,607,922 B2 | 8/2003 | LaBorde | |
| 6,611,634 B2 * | 8/2003 | Herron et al. | 385/12 |
| 6,629,057 B2 | 9/2003 | Zweig et al. | |
| 6,630,307 B2 | 10/2003 | Bruchez et al. | |
| 6,656,744 B2 | 12/2003 | Pronovost et al. | |
| 6,663,833 B1 | 12/2003 | Stave et al. | |
| 6,671,428 B1 | 12/2003 | Yang et al. | |
| 6,673,622 B1 | 1/2004 | Jina | |
| 6,673,630 B2 | 1/2004 | Albarella et al. | |
| 6,686,170 B1 * | 2/2004 | Flanders | G01N 33/558 435/4 |
| 6,713,271 B1 | 3/2004 | Feistel | |
| 6,732,917 B1 | 5/2004 | Benz et al. | |
| 6,750,963 B2 | 6/2004 | Sampas | |
| 6,855,561 B2 | 2/2005 | Jerome et al. | |
| 6,875,185 B2 | 4/2005 | Wong et al. | |
| 6,966,880 B2 | 11/2005 | Boecker et al. | |
| 7,378,285 B2 | 5/2008 | Lambotte et al. | |
| 7,521,260 B2 | 4/2009 | Petruno et al. | |
| 7,678,566 B2 | 3/2010 | Miyoshi et al. | |
| 8,043,867 B2 | 10/2011 | Petruno et al. | |
| 8,128,871 B2 | 3/2012 | Petruno et al. | |
| 9,243,997 B2 | 1/2016 | Petruno et al. | |
| 9,891,217 B2 | 2/2018 | Petruno et al. | |
| 9,989,527 B2 | 6/2018 | Petruno et al. | |
| 10,041,941 B2 | 8/2018 | Petruno et al. | |
| 2001/0034068 A1 | 10/2001 | Spivey et al. | |
| 2001/0035990 A1 | 11/2001 | Mok et al. | |
| 2002/0004246 A1 | 1/2002 | Daniels et al. | |
| 2002/0146844 A1 | 10/2002 | Pronovosi et al. | |
| 2002/0169439 A1 | 11/2002 | Flaherty | |
| 2002/0176927 A1 | 11/2002 | Kodas et al. | |
| 2003/0003601 A1 | 1/2003 | Some et al. | |
| 2003/0082516 A1 | 5/2003 | Straus | |
| 2003/0119202 A1 * | 6/2003 | Kaylor et al. | 436/514 |
| 2003/0119203 A1 | 6/2003 | Wei et al. | |
| 2003/0143580 A1 | 7/2003 | Straus | |
| 2003/0171697 A1 | 9/2003 | Smith et al. | |
| 2003/0174743 A1 | 9/2003 | Cliché et al. | |
| 2003/0175820 A1 | 9/2003 | Smith et al. | |
| 2003/0201176 A1 | 10/2003 | Mills et al. | |
| 2003/0207454 A1 | 11/2003 | Eyster et al. | |
| 2003/0222198 A1 | 12/2003 | Olszak et al. | |
| 2004/0012783 A1 | 1/2004 | Morokawa et al. | |
| 2004/0014202 A1 | 1/2004 | King et al. | |
| 2004/0018637 A1 * | 1/2004 | Polito et al. | 436/514 |
| 2004/0043502 A1 | 3/2004 | Song et al. | |
| 2004/0063219 A1 | 4/2004 | Bateman et al. | |
| 2004/0096169 A1 | 5/2004 | Sone et al. | |
| 2004/0151632 A1 | 8/2004 | Badley et al. | |
| 2004/0152209 A1 | 8/2004 | Zin et al. | |
| 2004/0214347 A1 | 10/2004 | LaBorde et al. | |
| 2005/0033196 A1 | 2/2005 | Alroy | |
| 2005/0037510 A1 | 2/2005 | Sharrock et al. | |
| 2005/0112703 A1 | 5/2005 | Song | |
| 2005/0130164 A1 | 6/2005 | Akimoto et al. | |
| 2005/0221504 A1 | 10/2005 | Petruno et al. | |
| 2005/0221505 A1 | 10/2005 | Petruno et al. | |
| 2006/0014302 A1 | 1/2006 | Martinez et al. | |
| 2006/0121625 A1 | 6/2006 | Clemens et al. | |
| 2006/0122782 A1 | 6/2006 | Petrilla et al. | |
| 2006/0126063 A1 | 6/2006 | Cluzel et al. | |
| 2006/0210435 A1 | 9/2006 | Alvavie et al. | |
| 2006/0216696 A1 | 9/2006 | Goguen | |
| 2006/0240541 A1 | 10/2006 | Petruno et al. | |
| 2006/0240568 A1 | 10/2006 | Petruno et al. | |
| 2007/0081920 A1 | 4/2007 | Murphy et al. | |
| 2007/0185679 A1 | 8/2007 | Petruno et al. | |
| 2007/0231922 A1 | 10/2007 | Petruno et al. | |
| 2009/0180925 A1 | 7/2009 | Petruno et al. | |
| 2009/0180926 A1 | 7/2009 | Petruno et al. | |
| 2009/0180927 A1 | 7/2009 | Petruno et al. | |
| 2009/0180928 A1 | 7/2009 | Petruno et al. | |
| 2009/0214383 A1 | 8/2009 | Petruno et al. | |
| 2012/0129272 A1 | 5/2012 | Petruno et al. | |
| 2014/0004624 A1 | 1/2014 | Petruno et al. | |
| 2016/0313254 A1 | 10/2016 | Petruno et al. | |
| 2017/0199183 A1 | 7/2017 | Petruno et al. | |

FOREIGN PATENT DOCUMENTS

| | | | |
|---|---|---|---|
| JP | H11108927 A | | 4/1999 |
| JP | 2001033454 A | | 2/2001 |
| JP | 2001066277 A | | 3/2001 |
| WO | WO 88/08534 | * | 11/1988 |
| WO | 95/13531 | | 5/1995 |
| WO | 99/41596 | | 8/1999 |
| WO | WO 2000/031538 | | 6/2000 |
| WO | 01/57502 | | 8/2001 |
| WO | 03/065009 | | 8/2003 |
| WO | WO 2003/098278 | | 11/2003 |
| WO | WO 2004/003527 | | 1/2004 |

* cited by examiner

ASSAY TEST STRIPS WITH MULTIPLE LABELS AND READING SAME

CROSS-REFERENCE TO RELATED APPLICATIONS

This application is a divisional of U.S. application Ser. No. 11/236,152, filed on Sep. 26, 2005, which is a continuation in part of U.S. application Ser. No. 11/112,807, filed on Apr. 22, 2005, each of which are incorporated by reference in their entirety.

BACKGROUND

Lateral flow assay test kits are currently available for testing for a wide variety of medical and environmental conditions or compounds, such as a hormone, a metabolite, a toxin, or a pathogen-derived antigen. FIG. 1 shows a typical lateral flow test strip 10 that includes a sample receiving zone 12, a labeling zone 14, a detection zone 15, and an absorbent zone 20 on a common substrate 22. These zones 12-20 typically are made of a material (e.g., chemically-treated nitrocellulose) that allows fluid to flow from the sample receiving zone 12 to the absorbent zone 22 by capillary action. The detection zone 15 includes a test region 16 for detecting the presence of a target analyte in a fluid sample and a control region 18 for indicating the completion of an assay test.

FIGS. 2A and 2B show an assay performed by an exemplary implementation of the test strip 10. A fluid sample 24 (e.g., blood, urine, or saliva) is applied to the sample receiving zone 12. In the example shown in FIGS. 2A and 2B, the fluid sample 24 includes a target analyte 26 (i.e., a molecule or compound that can be assayed by the test strip 10). Capillary action draws the liquid sample 24 downstream into the labeling zone 14, which contains a substance 28 for indirect labeling of the target analyte 26. In the illustrated example, the labeling substance 28 consists of an immunoglobulin 30 with a reflective particle 32 (e.g., a colloidal gold or silver particle). The immunoglobulin 30 specifically binds the target analyte 26 to form a labeled target analyte complex. In some other implementations, the labeling substance 28 is a non-immunoglobulin labeled compound that specifically binds the target analyte 26 to form a labeled target analyte complex.

The labeled target analyte complexes, along with excess quantities of the labeling substance, are carried along the lateral flow path into the test region 16, which contains immobilized compounds 34 that are capable of specifically binding the target analyte 26. In the illustrated example, the immobilized compounds 34 are immunoglobulins that specifically bind the labeled target analyte complexes and thereby retain the labeled target analyte complexes in the test region 16. The presence of the labeled analyte in the sample typically is evidenced by a visually detectable coloring of the test region 16 that appears as a result of the accumulation of the labeling substance in the test region 16.

The control region 18 typically is designed to indicate that an assay has been performed to completion. Compounds 35 in the control region 18 bind and retain the labeling substance 28. The labeling substance 28 typically becomes visible in the control region 18 after a sufficient quantity of the labeling substance 28 has accumulated. When the target analyte 26 is not present in the sample, the test region 16 will not be colored, whereas the control region 18 will be colored to indicate that assay has been performed. The absorbent zone 20 captures excess quantities of the fluid sample 24.

In the non-competitive-type of lateral flow assay test strip designs shown in FIGS. 2A and 2B, an increase in the concentration of the analyte in the sample results in an increase in the concentration of labels in the test region. Conversely, in competitive-type of lateral flow assay test strip designs, an increase in the concentration of the analyte in the fluid sample results in a decrease in the concentration of labels in the test region.

Although visual inspection of lateral flow assay devices of the type described above are able to provide qualitative assay results, such a method of reading these types of devices is unable to provide quantitative assay measurements and therefore is prone to interpretation errors. Automated and semi-automated lateral flow assay readers have been developed in an effort to overcome this deficiency.

What is needed are lateral flow assay test strips and systems and methods of reading such test strips that provide improved detection of different capture regions on the test strips, improved assay testing speed, and improved assay measurement sensitivity.

SUMMARY

In one aspect, the invention features an assay test strip that includes a flow path for a fluid sample and a sample receiving zone coupled to the flow path. The assay test strip additionally includes a test label that specifically binds a target analyte and a control label that is free of any specific binding affinity for the target analyte and has a different optical characteristic than the test label. A detection zone is coupled to the flow path downstream of the sample receiving zone and comprises an immobilized test reagent that specifically binds the target analyte and an immobilized control reagent that specifically binds the control label.

In another aspect, the invention features an assay test strip that includes a flow path for a fluid sample, a sample receiving zone coupled to the flow path, and a detection zone coupled to the flow path downstream of the sample receiving zone. The assay test strip additionally includes a test label that specifically binds a target analyte, and at least one non-specific-binding label that is free of any specific binding affinity for the target analyte. The detection zone comprises a first immobilized reagent that specifically binds the target analyte and a second immobilized reagent that specifically binds the test label, wherein each non-specific-binding label is free of any specific binding affinity for any of the immobilized reagents in the detection zone.

In another aspect, the invention features a diagnostic test system that includes an assay test strip and a reader. The assay test strip includes a detection zone and a flow path for a fluid sample along a lateral flow direction across the detection zone. The detection zone comprises a capture region characterized by a first dimension transverse to the lateral flow direction and a second dimension parallel to the lateral flow direction. The reader comprises an illumination system that is operable to focus a beam of light onto an area of the detection zone having at least one surface dimension at most equal to smallest of the first and second dimensions of the capture region.

The invention also features a diagnostic test method in accordance with which an assay test strip is received. The lateral flow assay test strip includes a detection zone and a flow path for a fluid sample along a lateral flow direction across the detection zone. The detection zone comprises a capture region characterized by a first dimension transverse to the lateral flow direction and a second dimension parallel to the lateral flow direction. A beam of light is focused onto one or more areas of the detection zone having at least one surface dimension at most equal to smallest of the first and second dimensions of the capture region. Light intensity measurements are obtained from the illuminated areas of the detection zone In another aspect, the invention features a diagnostic test system that includes a reader and a data analyzer. The reader is operable to obtain light intensity measurements from exposed regions of an assay test strip comprising a detection zone. The data analyzer is operable to perform operations comprising determining a test measurement value from light intensity measurements obtained from a test label bound to a region in the detection zone containing a first immobilized reagent, determining a compensation measurement value from light intensity measurements obtained from a compensation label different from the test label in one or more regions of the detection zone free of immobilized reagents that specifically bind the compensation label, and determining a parameter value from the test measurement value and the compensation measurement value.

The invention also features a diagnostic test method in accordance with which light intensity measurements are obtained from exposed regions of an assay test strip comprising a detection zone. A test measurement value is determined from light intensity measurements obtained from a region in the detection zone containing a test label bound to a first immobilized reagent. A compensation measurement value is determined from light intensity measurements obtained from a compensation label different from the test label in one or more regions of the detection zone free of immobilized reagents that specifically bind the compensation label. A parameter value is determined from the test measurement value and the compensation measurement value.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

I. Introduction

The embodiments that are described in detail below provide lateral flow assay test strips that include multiple labels and systems and methods for reading such test strips that provide improved detection of different capture regions on the test strips, improved assay testing speed, and improved assay measurement sensitivity.

The term "lateral flow assay test strip" encompasses both competitive and non-competitive types of lateral flow assay test strips. A lateral flow assay test strip generally includes a sample receiving zone and a detection zone, and may or may not have a labeling zone. In some implementations, a lateral flow assay test strip includes a sample receiving zone that is located vertically above a labeling zone, and additionally includes a detection zone that is located laterally downstream of the labeling zone.

The term "analyte" refers to a substance that can be assayed by the test strip. Examples of different types of analytes include organic compounds (e.g., proteins and amino acids), hormones, metabolites, antibodies, pathogen-derived antigens, drugs, toxins, and microorganisms (e.g., bacteria and viruses).

As used herein the term "label" refers to a substance that has specific binding affinity for an analyte and that has a detectable characteristic feature that can be distinguished from other elements of the test strip. The label may include a combination of a labeling substance (e.g., a fluorescent particle, such as a quantum dot) that provides the detectable characteristic feature and a probe substance (e.g., an immunoglobulin) that provides the specific binding affinity for the analyte. In some implementations, the labels have distinctive optical properties, such as luminescence (e.g., fluorescence)

or reflective properties, which allow regions of the test strip containing different labels to be distinguished from one another.

The term "reagent" refers to a substance that reacts chemically or biologically with a target substance, such as a label or an analyte.

The term "capture region" refers to a region on a test strip that includes one or more immobilized reagents.

The term "test region" refers to a capture region containing an immobilized reagent with a specific binding affinity for an analyte.

The term "control region" refers to a capture region containing an immobilized reagent with a specific binding affinity for a label.

II. General Architecture of the Diagnostic Test System

Figure 3:
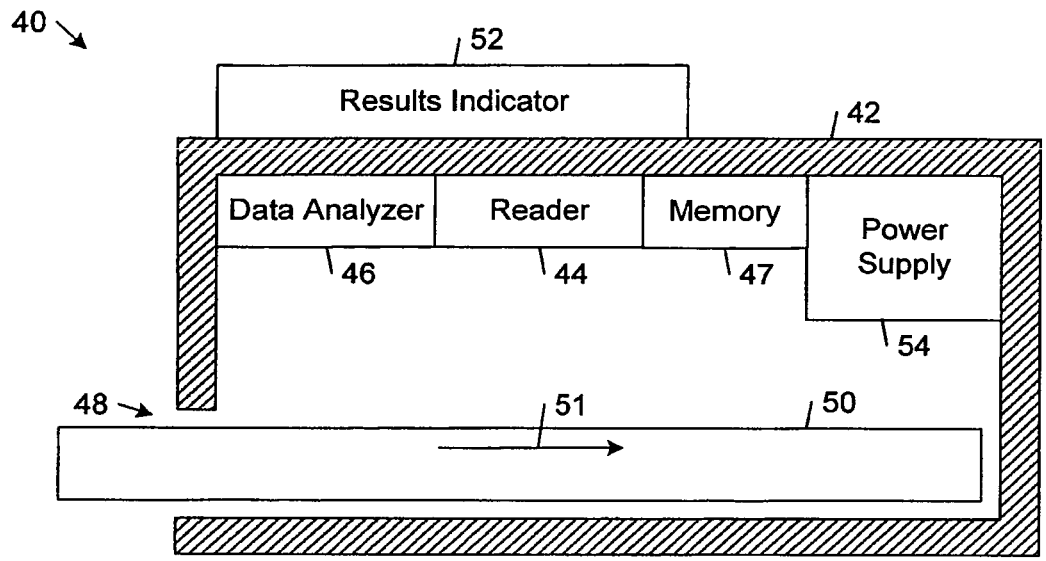
FIG. 3 is a block diagram of a test strip that is loaded into an embodiment of a diagnostic test system.

FIG. 3 shows an embodiment of a diagnostic test system 40 that includes a housing 42, a reader 44, a data analyzer 46, and a memory 47. The housing 42 includes a port 48 for receiving a test strip 50. When the test strip 50 is loaded in the port 48, the reader 44 obtains light intensity measurements from the test strip 50. In general, the light intensity measurements may be unfiltered or they may be filtered in terms of at least one of wavelength and polarization. The data analyzer 46 computes at least one parameter from one or more of the light intensity measurements. A results indicator 52 provides an indication of one or more of the results of an assay of the test strip 50. In some implementations, the diagnostic test system 40 is fabricated from relatively inexpensive components enabling it to be used for disposable or single-use applications.

Figure 1:
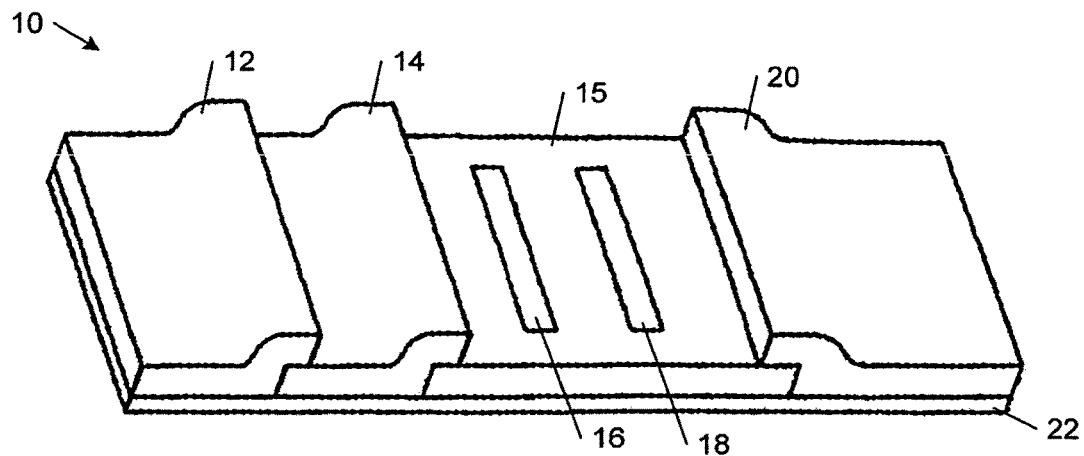
FIG. 1 is a diagrammatic view of a prior art implementation of a lateral flow assay test strip.
Figure 2A:
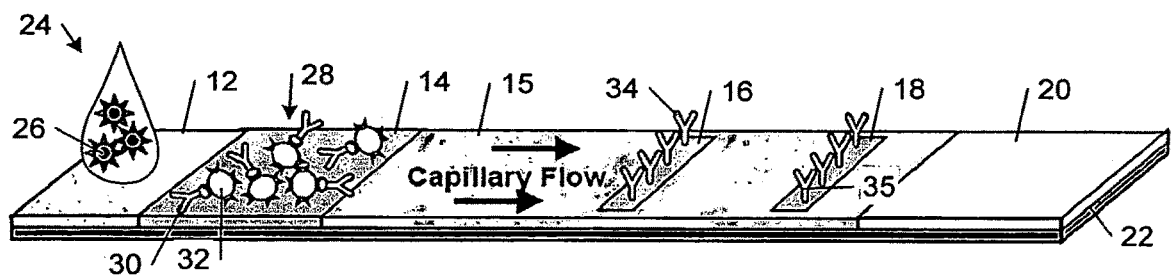
FIG. 2A is a diagrammatic view of a fluid sample being applied to a sample receiving zone of the lateral flow assay test strip shown in FIG. 1.
Figure 2B:
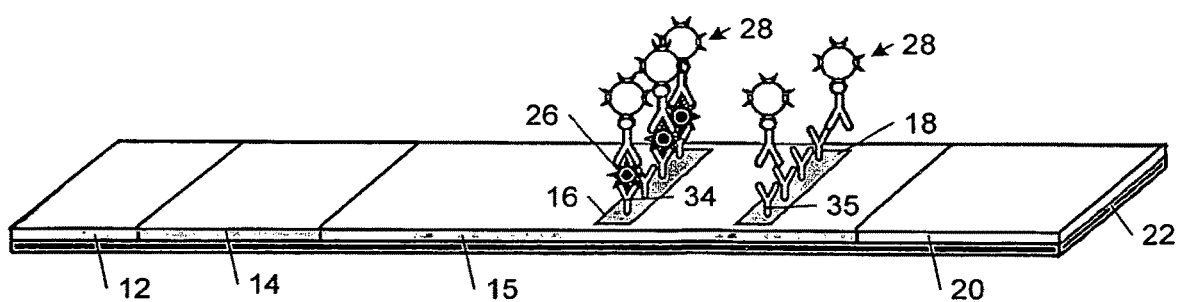
FIG. 2B is a diagrammatic view of the lateral flow assay test strip shown in FIG. 2A after the fluid sample has flowed across the test strip to an absorption zone.

The housing 42 may be made of any one of a wide variety of materials, including plastic and metal. The housing 42 forms a protective enclosure for the reader 44, the data analyzer 46, the power supply 54, and other components of the diagnostic test system 40. The housing 42 also defines a receptacle that mechanically registers the test strip 50 with respect to the reader 44. The receptacle may be designed to receive any one of a wide variety of different types of test strips 50, including test strips of the type shown in FIG. 1.

In the illustrated embodiments, each of the test strips 50 is a non-competitive type of lateral flow assay test strip that supports lateral flow of a fluid sample along a lateral flow direction 51 and includes a labeling zone containing a labeling substance that binds a label to a target analyte and a detection zone that includes at least one test region containing an immobilized substance that binds the target analyte. One or more areas of the detection zone, including at least a portion of the test region, are exposed for optical inspection by the reader 44. The exposed areas of the detection zone may or may not be covered by an optically transparent window.

In other embodiments, the test strips are competitive type of lateral flow assay test strips in which the concentrations of the label in the test region decreases with increasing concentration of the target analyte in the fluid sample. Some of these embodiments include a labeling zone, whereas others of these implementations do not include a labeling zone.

Some of these competitive lateral flow assay test strip embodiments include a labeling zone that contains a label that specifically binds target analytes in the fluid sample, and a test region that contains immobilized target analytes as opposed to immobilized test reagents (e.g., antibodies) that specifically bind any non-bound labels in the fluid sample.

In operation, the test region will be labeled when there is no analyte present in the fluid sample. However, if target analytes are present in the fluid sample, the fluid sample analytes saturate the label's binding sites in the labeling zone, well before the label flows to the test region. Consequently, when the label flows through the test region, there are no binding sites remaining on the label, so the label passes by and the test region remains unlabeled.

In other competitive lateral flow assay test strip embodiments, the labeling zone contains only pre-labeled analytes (e.g., gold adhered to analyte) and the test region contains immobilized test reagents with an affinity for the analyte. In these embodiments, if the fluid sample contains unlabeled analyte in a concentration that is large compared to the concentration of the pre-labeled analyte in the labeling zone, then label concentration in the test region will appear proportionately reduced.

The reader 44 includes one or more optoelectronic components for optically inspecting the exposed areas of the detection zone of the test strip 50. In some implementations, the reader 44 includes at least one light source and at least one light detector. In some implementations, the light source may include a semiconductor light-emitting diode and the light detector may include a semiconductor photodiode. Depending on the nature of the label that is used by the test strip 50, the light source may be designed to emit light within a particular wavelength range or light with a particular polarization. For example, if the label is a fluorescent label, such as a quantum dot, the light source would be designed to illuminate the exposed areas of the detection zone of the test strip 50 with light in a wavelength range that induces fluorescent emission from the label. Similarly, the light detector may be designed to selectively capture light from the exposed areas of the detection zone. For example, if the label is a fluorescent label, the light detector would be designed to selectively capture light within the wavelength range of the fluorescent light emitted by the label or with light of a particular polarization. On the other hand, if the label is a reflective-type label, the light detector would be designed to selectively capture light within the wavelength range of the light emitted by the light source. To these ends, the light detector may include one or more optical filters that define the wavelength ranges or polarizations axes of the captured light.

The data analyzer 46 processes the light intensity measurements that are obtained by the reader 44. In general, the data analyzer 46 may be implemented in any computing or processing environment, including in digital electronic circuitry or in computer hardware, firmware, or software. In some embodiments, the data analyzer 46 includes a processor (e.g., a microcontroller, a microprocessor, or ASIC) and an analog-to-digital converter. In the illustrated embodiment, the data analyzer 46 is incorporated within the housing 42 of the diagnostic test system 40. In other embodiments, the data analyzer 46 is located in a separate device, such as a computer, that may communicate with the diagnostic test system 40 over a wired or wireless connection.

In general, the results indicator 52 may include any one of a wide variety of different mechanisms for indicating one or more results of an assay test. In some implementations, the results indicator 52 includes one or more lights (e.g., light-emitting diodes) that are activated to indicate, for example, a positive test result and the completion of the assay test (i.e., when sufficient quantity of labeling substance 28 has accumulated in the control region). In other implementations, the results indicator 52 includes an alphanumeric display (e.g., a two or three character light-emitting diode array) for presenting assay test results.

A power supply 54 supplies power to the active components of the diagnostic test system 40, including the reader 44, the data analyzer 46, and the results indicator 52. The power supply 54 may be implemented by, for example, a replaceable battery or a rechargeable battery. In other embodiments, the diagnostic test system may be powered by an external host device (e.g., a computer connected by a USB cable).

Figure 4:
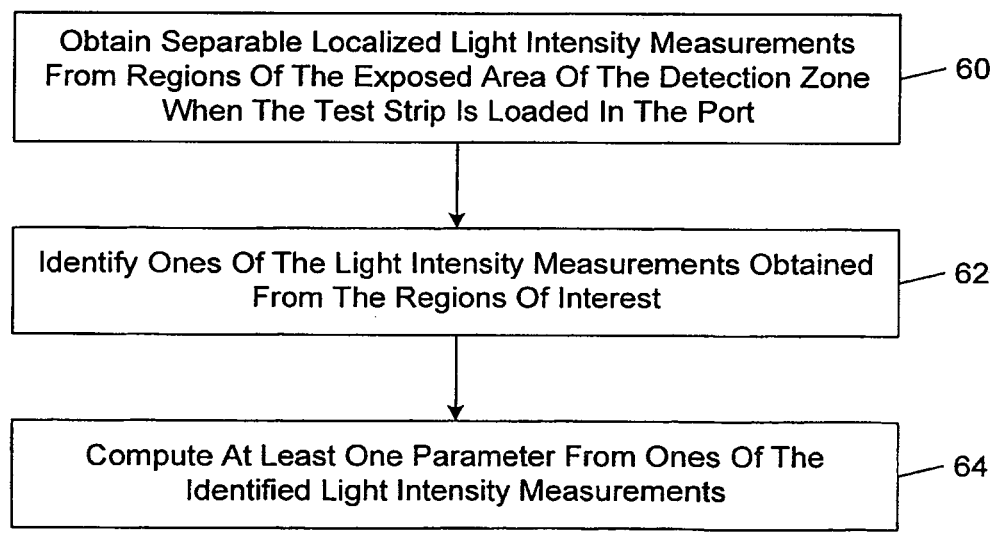
FIG. 4 is a flow diagram of an embodiment of a diagnostic test method.

FIG. 4 shows an embodiment of a diagnostic test method that is executable by implementations of the diagnostic test system 40 described below. In accordance with this method, the reader 44 obtains separable localized light intensity measurements from regions of the exposed area of the detection zone of the test strip 50 when the test strip 50 is loaded in the port 48 of the diagnostic test system 40 (block 60).

As used herein, the term "separable localized light intensity measurements" refers to the ability of the reader 44 transmit or record the light intensity measurements from respective localized regions of the test strip in a way that allows the data analyzer 46 to individually analyze each of the light intensity measurements.

In this embodiment, each of the separable localized regions from which the light intensity measurements are obtained by the reader 44 is characterized by at least one surface dimension that is smaller than the dimension of the exposed area of the detection zone that is transverse to the lateral flow direction. In some implementations, each of these localized regions has a surface dimension that is approximately the same size or smaller than the narrowest dimension of a region of interest in the detection zone (e.g., the test region, the control region, or a region of an immobilized labeled or unlabeled complex).

After the reader 44 has obtained light intensity measurements from such localized regions of interest in the detection zone (block 60), the data analyzer 46 identifies ones of the light intensity measurements obtained from the regions of interest (block 62). In this process, the data analyzer 46 isolates the measurements corresponding to regions of interest from the measurements corresponding to other regions of the test strip 50. The isolated measurements have higher signal-to-noise ratios than aggregated measurements that include measurements from regions outside of the regions of interest.

The data analyzer 46 computes at least one parameter from ones of the identified light intensity measurements (block 64). Exemplary parameters include peak intensity and aggregate intensity values. Since the measurements that are used to compute these parameters have higher signal-to-noise ratios, they characterize the region of interest with greater accuracy and, thereby, improve the results of the lateral flow assay.

III. Test Strips with Different Test and Control Labels and Reading the Same The embodiments that are described in this section provide lateral flow assay test strips that include different labels for test and control, as well as systems and methods of reading such test strips. The use of different test and control labels enables the test strip and the diagnostic test system to be designed in ways that improve the detectability of the test and control signals, improve assay testing speed, and improve assay measurement sensitivity.

A. Test Strips Having Different Test and Control Labels

In these embodiments, the labeling zone 14 includes a test label and a control label for each analyte to be assayed. In general, the test label and the associated control label have different respective detectable characteristics or properties. In some implementations, the test label fluoresces at a first characteristic wavelength and the control label fluoresces at a second characteristic wavelength different from the first characteristic wavelength. The test label may include, for example, quantum dots of a first type and the control label may include, for example, quantum dots of a second type. In some implementations, the quantum dots are nanometer sized semiconductor nanocrystals with fluorescent properties that are determined by their sizes. In this way, the fluorescence wavelengths of the quantum dots can be tuned by changing the sizes of the quantum dots.

The test label is bound by an immobilized test reagent in the detection zone 15 that has a specific binding affinity for the test label. The control label is bound by an immobilized control reagent in the detection zone 15 that has a specific binding affinity for the control label. The different test and control labels may be immobilized in the detection zone 15 of the test strip in separate discrete capture regions or in the same test-and-control capture region. In general, the test and control regions may have any shape, including rectangular and non-rectangular shapes.

Figure 5A:
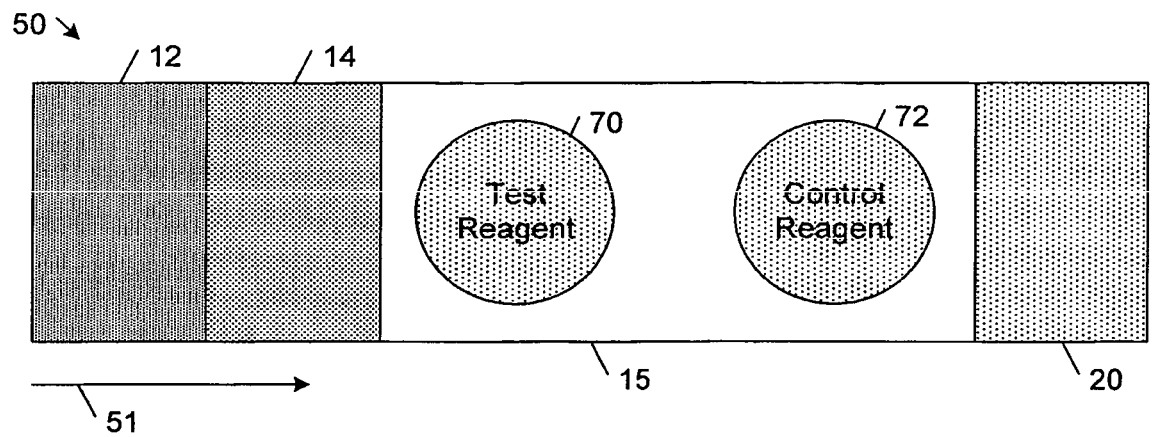
FIG. 5A is a diagrammatic top view of an embodiment of a test strip that includes separate plano-circular test and control capture regions.

For example, FIG. 5A shows an embodiment of the test strip 50 that has a test region 70 that contains an immobilized test reagent and a separate and distinct control region 72 that contains an immobilized control reagent. In the illustrated embodiment, each of the test and control regions 70, 72 has a respective plano-circular shape in the plane of the surface of the detection zone 15. Such a shape allows a suitably configured reader 44 to project an illumination beam onto a plano-circular area of the detection zone 15 that substantially corresponds to the test-and-control regions 70, 72 in size and shape. In this way, the light intensity measurements that are obtained from the test and control labels may have higher signal-to-noise levels, increased measurement sensitivity, and reduced incidence of erroneous results for low concentrations of analytes.

Figure 5B:
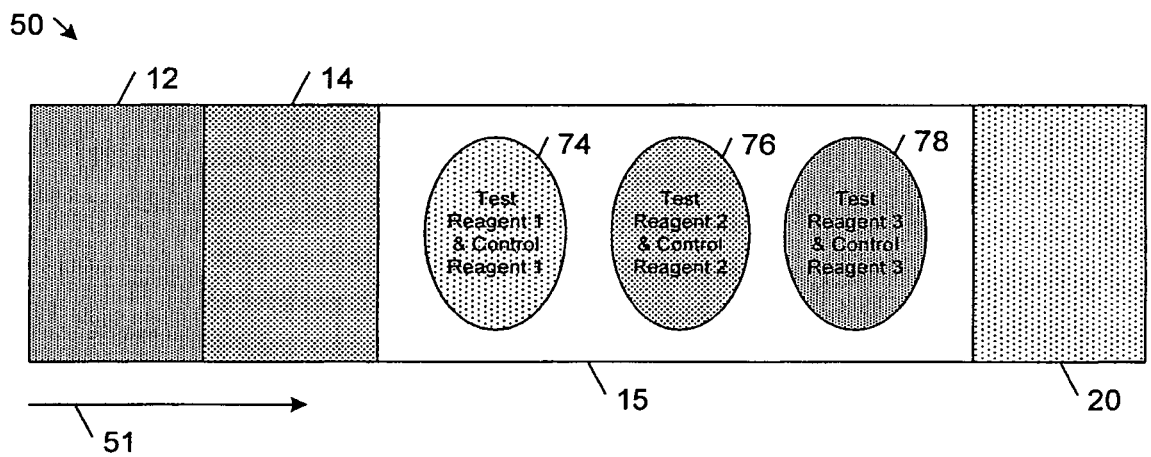
FIG. 5B is a diagrammatic top view of an embodiment of a test strip that includes three combined test-and-control capture regions each of which has a plano-elliptical shape.

FIG. 5B shows an exemplary implementation of the test strip 50 that includes three combined test-and-control regions 74, 76, 78. Each of the test-and-control regions 74-78 includes a respective immobilized test reagent and a respective immobilized control reagent that are intermixed in the same region of the detection zone 15. Each test reagent has a specific binding affinity for a respective target analyte that is specifically bound by a respective test label in the labeling zone 14 and each control reagent has a specific binding affinity for a respective control label in the labeling zone 14. In some implementations, the test label and the control label in each capture region 74-78 fluoresce at different characteristic wavelengths, enabling their fluorescent emissions to be distinguished using wavelength separation techniques (e.g., diffractive optics and optical filters).

In the test strip embodiment shown in FIG. 5B, each test-and-control region 74-78 has a respective plano-elliptical shape in the plane of the surface of the detection zone 15. Such a shape allows a suitably configured reader 44 to project an illumination beam onto a plano-elliptical area of the detection zone 15 that substantially corresponds to the test-and-control regions 74-78 in size and shape. In this way, the light intensity measurements that are obtained from the test and control labels may have higher signal-to-noise levels, increased measurement sensitivity, and reduced the incidence of erroneous results for low concentrations of analytes.

Figure 6:
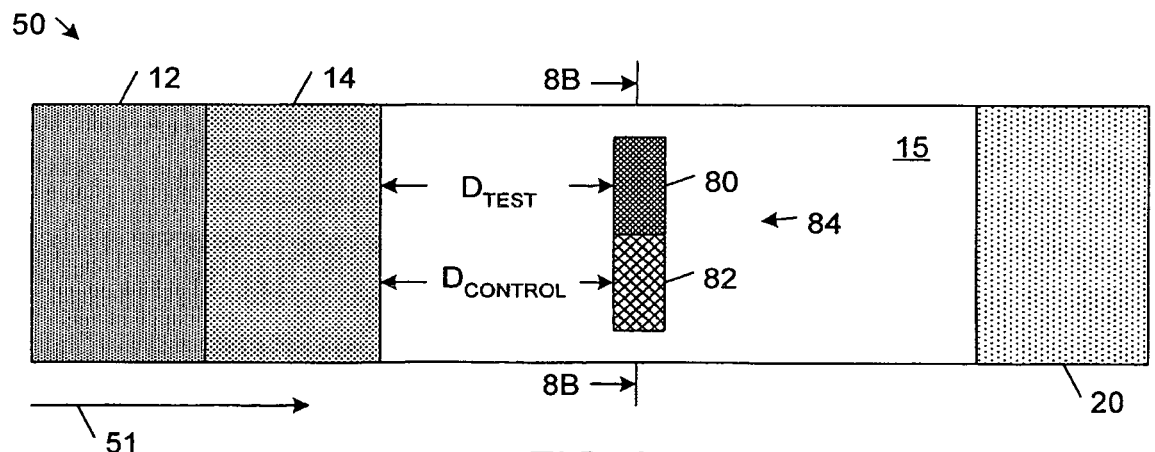
FIG. 6 is a diagrammatic top view of an embodiment of a test strip that includes a capture region that has a test reagent sub-region and a control reagent sub-region that are equidistant from a labeling zone.

FIG. 6 shows an implementation of the test strip 50 in which the test reagent and the control reagent are immobilized in respective sub-regions 80, 82 of a combined test-and-control region 84. In the illustrated embodiment, the test reagent sub-region 80 and the control reagent sub-region 82 are equidistant from the labeling zone 14 (i.e., $D_{TEST}=D_{CONTROL}$). The test reagent sub-region 80 and the control reagent sub-region 82 also are equidistant from the sample receiving zone 12. In this implementation, the fluid sample need only flow through one capture location along the lateral flow direction before the test and control results can be determined. Therefore, the assay testing speed with respect to this test strip implementation may be faster than the assay testing speed for implementations in which separate test and control regions are located at different locations in the lateral flow direction 51.

B. Illuminating the Different Test and Control Labels

The illumination source of the reader 44 may be constructed and arranged to focus or scan a light beam onto an area of the detection zone that is sized and shaped so that the light reflected or fluorescing from the test and control labels easily may be segmented from other regions of the detection zone 15. In some embodiments, the capture regions (i.e., the separate test and control regions and the combined test-and-control regions) may have non-rectangular shapes, which allow relatively inexpensive optical components to be used to project light beams onto areas of the detection zone 15 that substantially correspond to the capture regions in size and shape. In this way, the aggregate signals that are generated by the detection system of the reader 44 largely corresponds to light respectively reflecting or fluorescing from the illuminated capture regions and therefore have higher signal-to-noise ratios than comparable measurements obtained as a result of illumination of areas that do not substantially correspond to the shapes of the capture regions.

Figure 7A:
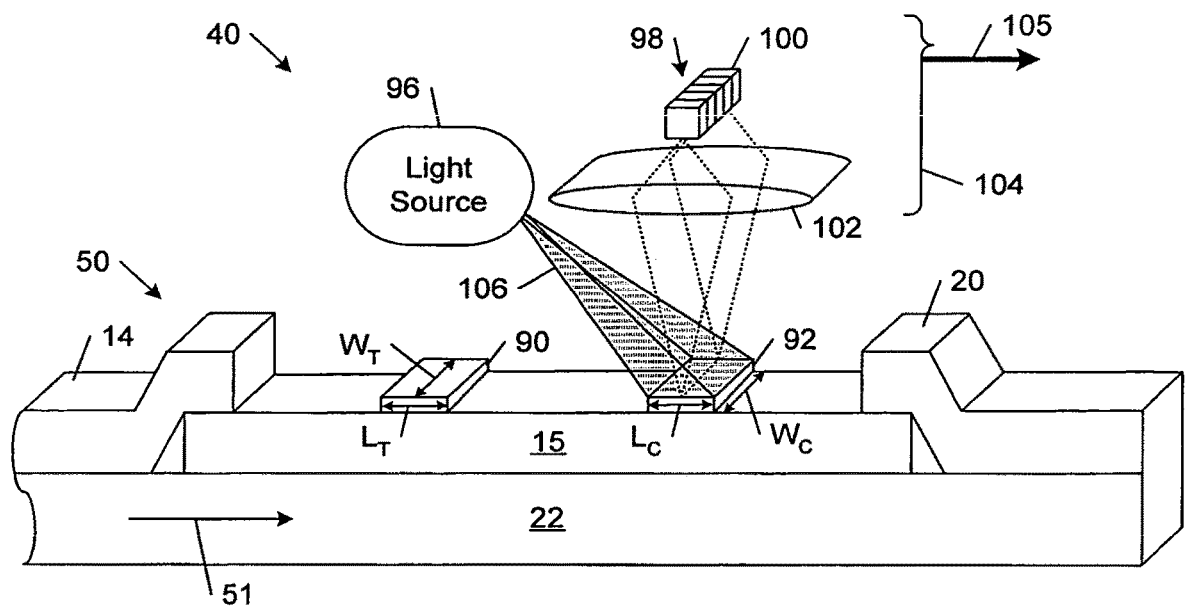
FIG. 7A is a diagrammatic view of an implementation of the diagnostic test system shown in FIG. 3 that includes an illumination system focusing a light beam onto a capture region and a linear light detector array obtaining light intensity measurements from regions of a test strip.

FIG. 7A shows an implementation of the test strip 50 and an implementation of the diagnostic test system 40.

The test strip includes a test region 90 that is separate and distinct from the control region 92. The test region 90 includes an immobilized test reagent that specifically binds a target analyte and the control region 92 includes an immobilized control reagent that specifically binds a label. Each of the test and control capture regions 90, 92 is characterized by a first dimension ($W_T$, $W_C$) transverse to the lateral flow direction 51 and a second dimension ($L_T$, $L_C$) parallel to the lateral flow direction 51.

The diagnostic test system 40 includes a light source 96, a linear array 98 of light detectors 100, and a lens 102. In this implementation, the diagnostic test system 40 additionally includes a mechanism (not shown) for imparting relative motion between the optical inspection components 104 (e.g., the light source 96, the lens 102, and the linear light detector array 98) and the test strip 50. The motion-imparting mechanism may be any one of a wide variety of different mechanisms, including a motorized carriage that moves the optical inspection components relative to the test strip 50 on a pair of rails, and one or more motorized drive wheels that move the test strip 50 relative to the optical inspection components 104. In the illustrated embodiment, the optical inspection components 104 are shown moving relative to the test strip 50 in the direction of arrow 105 (i.e., in the lateral flow direction 51).

The linear light detector array 98 is oriented in a direction transverse to the direction of motion of the optical inspection components 104.

In implementations in which the test and control labels are distinguishable by, for example, their different wavelengths of fluorescent emission, the test and control regions 90, 92 may coincide. In these implementations, multiple optical filters or a single tunable optical filter may be used to distinguish the light that is received from the test and control labels.

In operation, the light source 96 illuminates an area of the exposed portion of the detection zone 15 with a beam of light 106 as the optical inspection components 104 are moved relative to the test strip 50. The illuminating light may be broadband or narrowband and may be polarized or non-polarized. The light source 96 focuses the light beam 106 onto the detection zone 15 with a shape having at least one surface dimension that is at most the smaller of characteristic dimensions ($W_T$, $L_T$, $W_C$, $L_C$) of the test and control capture regions 90, 92. In the illustrated embodiment, the light beam 106 illuminates an area that substantially corresponds to each of the capture regions in size and shape.

The linear light detector array 98 obtains separable localized light intensity measurements from a narrow portion of the illuminated region of the detection zone 15. In general, the light intensity measurements may be unfiltered or they may be filtered in terms of wavelength or polarization. The light detector array 98 may be synchronized with the light source 96. In general, the light detector array 98 may measure light intensity while the detection zone 15 is being illuminated or after the light source 96 has illuminated the detection zone 15. Light reflected or fluorescing from the detection zone 15 is focused by the lens 102 onto the individual light detectors 100 of the light detector array 98. Each of the light detectors 100 receives light from a respective localized region of the detection zone 15. That is, each light detector 100 is able to resolve or separably image a respective localized region of the detection zone 15. The light detectors 100 produce signals representative of the amount of light received from the respective localized regions. These signals may be stored in a memory or they may be transmitted to the data analyzer 46 for processing.

When the illuminated area of the detection zone 15 coincides with one of the capture regions 90, 92, the aggregate signal that is generated by the light detector array 98 largely corresponds to light reflecting or fluorescing from the illuminated capture region and therefore has a higher signal-to-noise ratio than comparable measurements obtained from larger areas of the detection zone 15. The test strip 50 may include position markers or other features that may be used by the diagnostic test system 40 to determine when the illuminated area of the detection zone 15 coincides with one of the capture regions 90, 92. A description of exemplary types of alignment features may be obtained from U.S. patent application Ser. No. 11/280,640, filed Nov. 16, 2005, by Patrick T. Petruno et al. and entitled "ASSAY TEST STRIPS AND READING SAME".

The data analyzer 46 (FIG. 3) is operable to process the signals that are generated by the individual light detectors 100 of the linear array 98 to identify the ones of the light intensity measurements that are obtained from the regions of interest (e.g., the test region 90 and the control region 92). In some implementations, the surface of the detection zone 15 is substantially homogeneous in the direction transverse to the lateral flow direction. In these implementations, the signals from the light detectors in the linear array 98 may be aggregated without substantial loss of information.

Figure 7B:
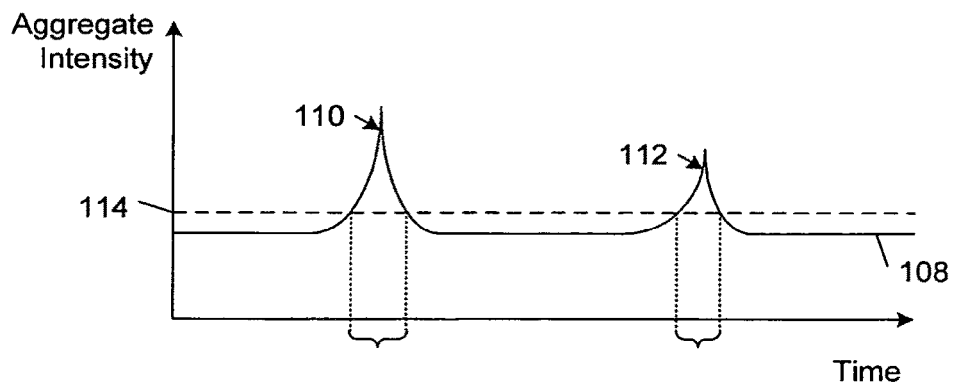
FIG. 7B is an exemplary graph of aggregate light intensity obtained by the linear light detector array shown in FIG. 7A plotted as a function of time.

FIG. 7B shows an exemplary graph 108 of the aggregated intensity measurements that are produced by the linear light detector array 98 plotted as a function of time. In this example, the graph 108 includes higher intensity aggregate intensities 110, 112 when the light detectors 100 in the array 98 are positioned over the test region 90 and the control region 92. With respect to this example, the data analyzer 46 may identify the light intensity measurements that are obtained from the test region 90 and the control region 92 by thresholding the graph 108 at an intensity threshold level 114. The light intensity measurements that are above the threshold level 114 are identified as having come from the test region 90 and the control region 92. Additional information, such as the relative times the identified ones of the light intensity measurements were obtained, may be used by the data analyzer 46 to correlate the identified light intensity measurements with the test region 90 and the control region 92.

Figure 8:
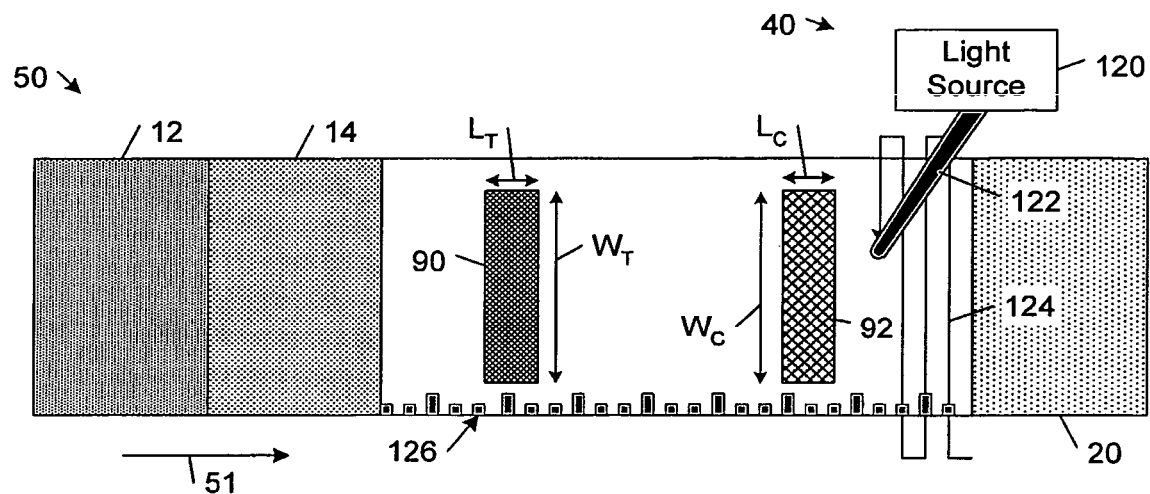
FIG. 8 is a diagrammatic top view of an implementation of the diagnostic test system shown in FIG. 3 that includes a light source scanning a light beam over regions of a test strip.

FIG. 8 shows an implementation of the diagnostic test system 40 that includes a light source 120 that is operable to scan a light beam 122 across the exposed area of the detection zone 15. The light source 120 focuses the light beam 122 onto the detection zone 15 with a shape having at least one surface dimension that is at most the smaller of characteristic dimensions ($W_T$, $L_T$, $W_C$, $L_C$) of the test and control capture regions 90, 92. In the illustrated embodiment, the surface area illuminated by the light beam 122 has a circular dimension that is smaller than each of the characteristic dimensions ($W_T$, $L_T$, $W_C$, $L_C$) of the test and control regions 90, 92. The light beam 122 may be broadband or narrowband and may be polarized or non-polarized.

In general, the light source 120 may scan the light beam 122 across the exposed area of the detection zone 15 along any path that includes the test region 90 and the control region 92, including in a direction transverse to the lateral flow direction and a direction parallel to the lateral flow direction. In the illustrated embodiment, the light source 120 scans the light beam 122 along a circuitous zigzag path 124 across the exposed area of the detection zone 15. In some implementations, the light source 120 includes a light emitter, such as a light-emitting diode or a laser, and one or more optical components (e.g., one or more lenses and a rotating mirror) for shaping and scanning the emitted light to produce the beam 122.

In the implementation shown in FIG. 8, the diagnostic test system 40 may obtain separable localized light intensity measurements using any type of single-element or multi-element light detector that has a field of view that encompasses the path of the light beam 122 across the exposed area of the detection zone 15 or that tracks the localized regions of the detection zone 15 as they are illuminated by the light beam 122. The light intensity measurements may be unfiltered or they may be filtered in terms of wavelength or polarization. The light detector array may be synchronized with the light source. In general, the light detector array may measure light intensity while individual separable localized regions of the detection zone 15 are being illuminated or after the light source has illuminated the individual separable localized regions of the detection zone 15. Because the light beam 122 illuminates only a single localized region of the detection zone 15 at a time, the light obtained by the light detector corresponds to the light reflected or fluorescing from the illuminated localized region. Therefore, each data point of the signal that is generated by the light detector correlates with a respective localized region and has a higher signal-to-noise ratio than comparable measurements obtained from larger regions of the detection zone 15.

The data analyzer 46 (FIG. 3) is operable to process the signals that are generated by the light detectors to identify the ones of the light intensity measurements that are obtained from the regions of interest (e.g., the test region 90 and the control region 92). For example, in some implementations, the data analyzer 46 may identify the light intensity measurements that are obtained from the test region 90 and the control region 92 by thresholding the time-varying light intensity measurement signal that is generated by the light detector. The ones of the light intensity measurements that are above the threshold level are identified as having come from the test region 90 and the control region 92. Additional information, such as the relative times the identified ones of the light intensity measurements were obtained, may be used by the data analyzer 46 to correlate the identified light intensity measurements with the test region 90 and the control region 92.

In the implementation of the test strip 50 that is shown in FIG. 8, a set of regularly spaced position markers 126 are located along one edge of the test strip 50. The position markers 126 include features that have a different optical characteristic (e.g., reflectivity or fluorescence) than the surface of the test strip 50. As a result, the measurements obtained near the edge of the test strip 50 vary in intensity in accordance with the pattern of the position markers 126. In this way, the position markers encode positions along the test strip 50 in the lateral flow direction. The data analyzer 46 may determine the encoded positions along the lateral flow direction by incrementing a position counter with each intensity variation cycle (e.g., peak-to-valley) in the light intensity measurements obtained from the edge of the detection zone 15. In these implementations, the data analyzer 46 correlates the light intensity measurements with the positions along the test strip 50 in the lateral flow direction 51. The location correlation information may be stored in a lookup table that is indexed by the position counter value. Based on this information and predetermined information correlating the locations of the regions of interest with the light intensity contrast pattern produced by the position markers 126, the data analyzer 46 can identify the ones of the light intensity measurements corresponding to the regions of interest.

C. Detecting Light from the Different Test and Control Labels

In some implementations, the test label fluoresces at a first characteristic wavelength and the control label fluoresces at a second characteristic wavelength different from the first characteristic wavelength. Implementations of the reader 44 may include a detection system that is constructed and arranged to segment the light reflected or fluorescing from the test and control labels from each other and from other regions of the detection zone 15.

Figure 9:
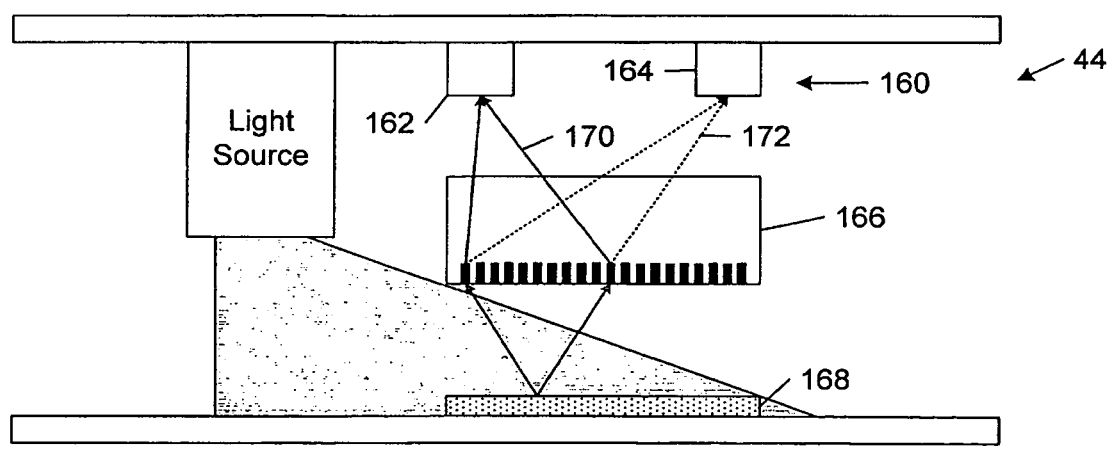
FIG. 9 is a diagrammatic side view of an implementation of the diagnostic test system shown in FIG. 3.

FIG. 9 shows an implementation of the reader 44 that may be used to separate the fluorescent light emitted from the test and control labels that are bound in separate test and control regions (see, e.g., FIG. 5A) or in the same test-and-control region (see, e.g., FIGS. 5B and 6). The reader 44 obtains separable localized light intensity measurements using a light detector array 160, wherein each individual detector element 162, 164 is the target of a specific characteristic wavelength of light that is separated and steered by a diffractive lens 166. In the illustrated example, the different test and control labels are immobilized in a combined test-and-control region 168. The light 170 from the immobilized test label is steered by the diffractive lens 166 to the detector element 162, whereas the light from the immobilized control label is steered by the diffractive lens to the detector element 164. In the implementation shown in FIG. 9, each detector element 162, 164 additionally may include a respective optical filter with narrow passbands selected to preferentially transmit light from the test and control labels, respectively.

In some embodiments, the reader 44 includes first and second optical filters that are constructed and arranged to filter light received by first and second light detectors (or first and second regions of a shared light detector array). The first optical filter selectively transmits light within a first wavelength range that encompasses the first characteristic wavelength and excludes the second characteristic wavelength. The second optical filter selectively transmits light within a second wavelength range that encompasses the second characteristic wavelength and excludes the first characteristic wavelength. In some implementations, the first and second wavelength ranges substantially correspond to the predominant fluorescent emission spectra of the test and control labels. In this way, the first and second optical filters are able to reduce noise that might be caused by light from elements other than the test and control labels, respectively. In some implementations, the optical filters are polarized to selectively transmit polarized light that is received from the test and control labels.

With respect to test strip implementations in which the different test and control labels are immobilized in separate discrete test and control regions in the detection zone 15, the test and control labels may be assayed by embodiments of the diagnostic test system 40 in which the positions of the detector components are correlated with the positions of the test and control regions to improve the ability to detect the test and control regions of the test strip.

Figure 10:
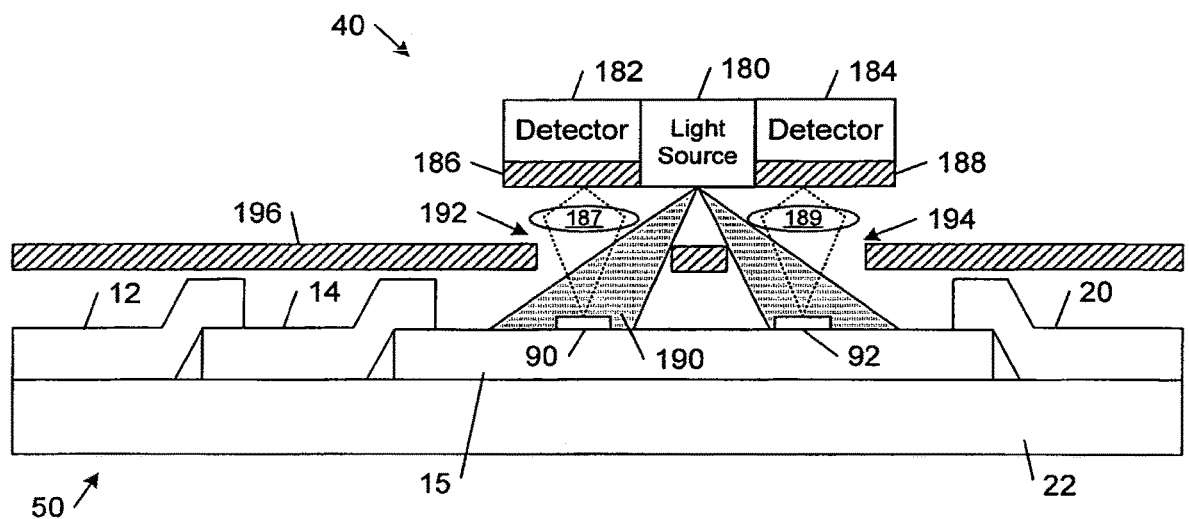
FIG. 10 is a diagrammatic view of an implementation of the diagnostic test system shown in FIG. 3 that includes first and second imaging devices that are respectively disposed directly over first and second capture regions of a test strip.

For example, FIG. 10 shows an embodiment of the test strip 50 that includes a test region 90 and a control region 92, which respectively contain immobilized test and control reagents. The test and control reagents respectively have specific binding affinity for test and control labels in the labeling zone 14. In some implementations, the test label fluoresces at a first characteristic wavelength and the control label fluoresces at a second characteristic wavelength different from the first characteristic wavelength. The test label may include, for example, quantum dots of a first type and the control label may include, for example, quantum dots of a second type.

FIG. 10 also shows an implementation of the diagnostic test system 40 that includes a light source 180 and a pair of light detectors 182, 184. The light source 180 may be implemented by one or more light-emitting diodes that generate a relatively broad beam of light that illuminates the regions of interest in the detection zone 15. The light detectors 182, 184 may be implemented by single-element light detectors or multi-element light detectors that are disposed directly over the test region 90 and the control region 92 when the test strip 50 is loaded within the port 48 of the diagnostic test system 40. The light detectors 182, 184 respectively include first and second optical filters 186, 188. The first optical filter 186 selectively transmits light within a first wavelength range that encompasses the first characteristic wavelength and excludes the second characteristic wavelength. The second optical filter 188 selectively transmits light within a second wavelength range that encompasses the second characteristic wavelength and excludes the first characteristic wavelength. In some implementations, the first and second wavelength ranges substantially correspond to the predominant fluorescent emission spectra of the test and control labels. In this way, the optical filters 186, 188 are able to reduce noise that might be caused by light from elements other than the test and control labels, respectively. In some implementations, the optical filters 186, 188 are polarized to selectively transmit polarized light received from the test and control labels.

In operation, the light source 180 illuminates the test region 90 and the control region 92 with light 190. The illuminating light 190 may be broadband or narrowband and may be polarized or non-polarized. The light detectors 182, 184 obtain separable localized light intensity measurements from the illuminated regions of the detection zone 15. The detectors 182, 184 may be synchronized with the light source 180. In general, the light detectors 182, 184 may measure light intensity while the detection zone 15 is being illuminated or after the light source 180 has illuminated the detection zone 15. Light reflected or fluorescing from the test region 90 and the control region 92 is focused by the lenses 187, 189 onto the light detectors 182, 184, respectively. In this way, the light detectors 182, 184 are able to resolve or separably image the test region 90 and the control region 92. The light detectors 182, 184 produce signals representative of the amount of light received from the test region 90 and the control region 92. If the light detectors 182, 184 are implemented by single-element detectors, the signals represent total or aggregate amounts of light received from the test region 90 or the control region 92. If the light detectors 182, 184 are implemented by multi-element detectors, the signals represent the amounts of light received from localized areas of the test region 90 and the control region 92. The signals that are generated by the light detectors 182, 184 may be stored in a memory or they may be transmitted to the data analyzer 46 for processing.

In some implementations, the light reflected or fluorescing from the test region 90 and the control region 92 is preferentially transmitted through apertures 192, 194 in an aperture plate 196, whereas light from other regions of the test strip 50 are substantially blocked by the aperture plate 196. As a result, the signals that are generated by the light detectors 182, 184 have higher signal-to-noise ratios than comparable measurements obtained from larger regions of the detection zone 15. In addition, the light obtained by the light detectors 182, 184 substantially corresponds to the light reflected or fluorescing from the test region 90 and the control region 92, respectively. Therefore, the signals that are generated by the light detectors 182, 184 correlate with the test region 90 and the control region 92, respectively, and the data analyzer 46 can identify the ones of the light intensity measurements that are obtained from the test region 90 and the control region 92 directly. That is, the light intensity measurements generated by the light detector 182 are obtained from the test region 90 and the light intensity measurements generated by the light detector 184 are obtained from the control region 92.

Figure 11:
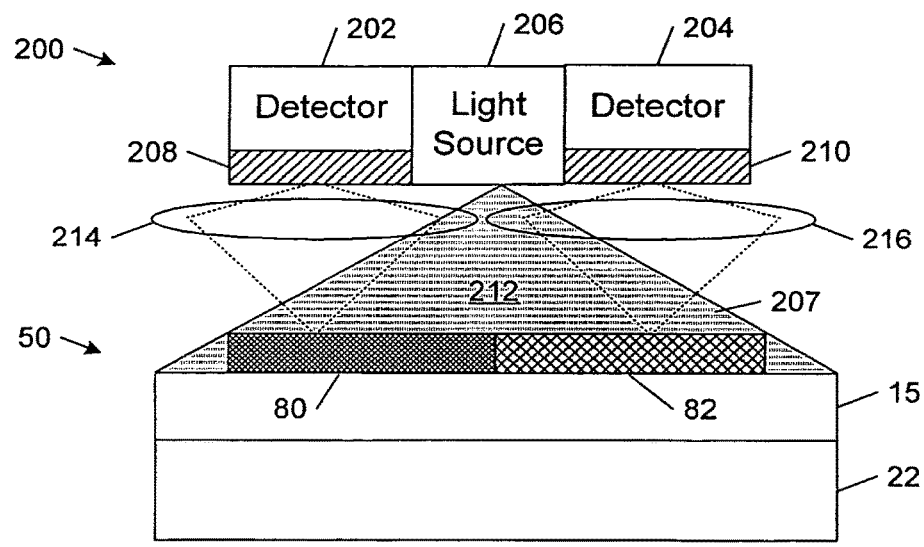
FIG. 11 is a diagrammatic side view of an implementation of the diagnostic test system shown in FIG. 3 obtaining measurements from the test strip shown in FIG. 6.

FIG. 11 shows an implementation of the diagnostic test system 40 that includes an illumination system 200, which has a first detector 202, a second detector 204, and a light source 206.

The light source 206 may be implemented by one or more light-emitting diodes that generate a relatively broad beam of light 207 that illuminates the regions of interest in the detection zone 15. The light detectors 202, 204 may be implemented by single-element light detectors or multi-element light detectors that are disposed directly over the test reagent sub-region 80 and the control reagent sub-region 82 when the test strip 50 is loaded within the port 48 of the diagnostic test system 40. The light detectors 202, 204 respectively include first and second optical filters 208, 210. The first optical filter 208 selectively transmits light within a first wavelength range that encompasses the first characteristic wavelength and excludes the second characteristic wavelength. The second optical filter 210 selectively transmits light within a second wavelength range that encompasses the second characteristic wavelength and excludes the first characteristic wavelength. In some implementations, the first and second wavelength ranges substantially correspond to the predominant fluorescent emission spectra of the test and control labels. In this way, the optical filters 208, 210 are able to reduce noise that might be caused by light from elements other than the test and control labels, respectively. In some implementations, the optical filters 208, 210 are polarized to selectively transmit polarized light received from the test and control labels.

In operation, the light source 206 illuminates the test reagent sub-region 80 and the control reagent sub-region 82 with light 212. The illuminating light 207 may be broadband or narrowband and may be polarized or non-polarized. The light detectors 202, 204 obtain separable localized light intensity measurements from the illuminated regions of the detection zone 15. The detectors 202, 204 may be synchronized with the light source 206. In general, the light detectors 202, 204 may measure light intensity while the detection zone 15 is being illuminated or after the light source 200 has illuminated the detection zone 15. Light reflected or fluorescing from the test reagent sub-region 80 and the control reagent sub-region 82 is focused by the lenses 214, 216 onto the light detectors 202, 204, respectively. In this way, the light detectors 202, 204 are able to resolve or separably image the test reagent sub-region 80 and the control reagent sub-region 82. The light detectors 202, 204 produce signals representative of the amount of light received from the test reagent sub-region 80 and the control reagent sub-region 82. If the light detectors 202, 204 are implemented by single-element detectors, the signals represent total or aggregate amounts of light received from the test reagent sub-region 80 or the control reagent sub-region 82. If the light detectors 202, 204 are implemented by multi-element detectors, the signals represent the amounts of light received from localized areas of the test reagent sub-region 80 and the control reagent sub-region 82. The signals that are generated by the light detectors 202, 204 may be stored in a memory or they may be transmitted to the data analyzer 46 for processing.

IV. Test Strips with Non-Specific-Binding Labels and Reading the Same

The embodiments that are described in this section provide lateral flow assay test strips that include one or more compensation labels that are not specifically bound by the regions from which compensation measurements are made. A compensation label may bind non-specifically to the capture and non-capture regions of the detection zone 15, or it may bind specifically to some but not all of the regions of the detection zone 15. These embodiments include implementations of the diagnostic test system 40 that are designed to compensate for non-specific binding effects in parameter values that are derived from light intensity measurements of test and/or control labels based on light intensity measurements obtained from the compensation labels. These embodiments may be implemented with respect to both competitive and non-competitive types of lateral flow assay test strips embodiments.

Figure 12A:
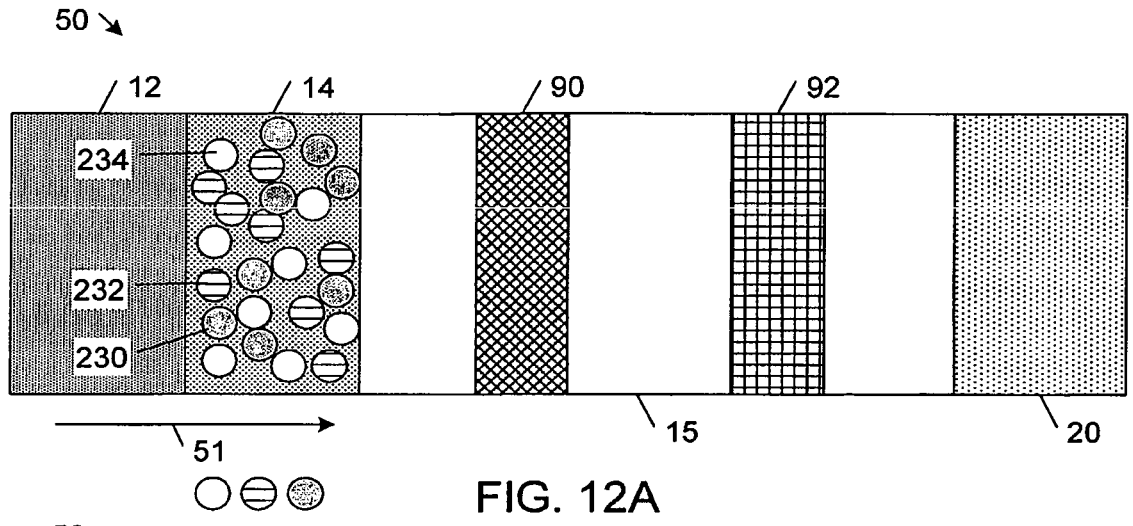
FIG. 12A is a diagrammatic top view of an embodiment of a test strip that has a labeling zone that includes a test label and a non-specific-binding label.
Figure 12B:
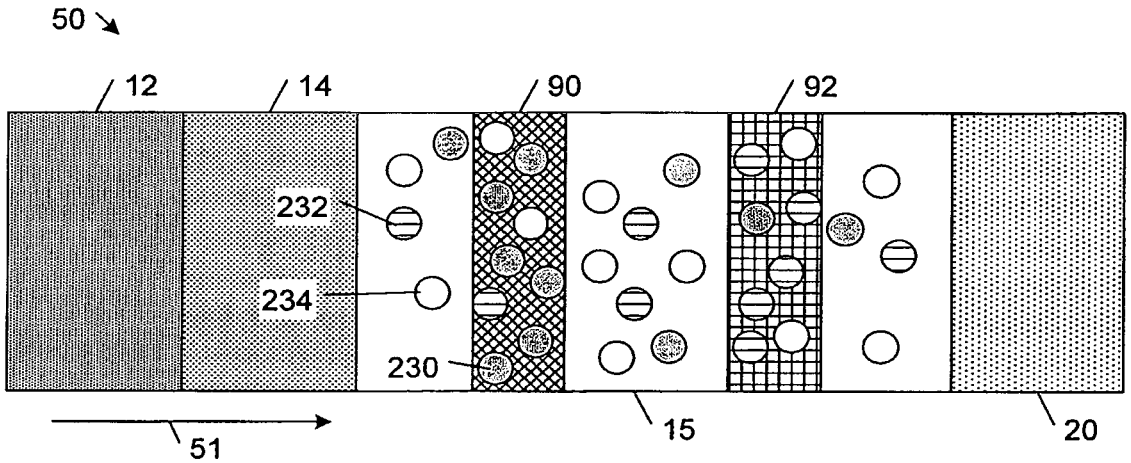
FIG. 12B is a diagrammatic top view of the test strip embodiment shown in FIG. 12A after a fluid sample has flowed through the test strip.

FIGS. 12A and 12B show an implementation of the test strip 50 in which the labeling zone 14 includes a test label 230, a control label 232, and a non-specific-binding compensation label 234. The detection zone 15 includes a test region 90 that includes an immobilized test reagent that specifically binds a target analyte, and a control region 92 that includes an immobilized control reagent that specifically binds the control label. In some implementations, each of the labels 230-234 fluoresces at a different characteristic wavelength. The labels 230-234 may include, for example, quantum dots of different respective types.

FIG. 12A shows the test strip 50 before a fluid sample has been applied to the sample receiving zone 12. FIG. 12B shows the test strip 50 after a fluid sample, which was applied to the sample receiving zone 12, has flowed along the flow path in the lateral flow direction 51 from the sample receiving zone 12 to the absorbent zone 20. In the illustrated example, the applied fluid sample contained the target analyte that is specifically bound by the test label and the test reagent.

As shown in FIG. 12B, the test label 230 accumulates predominantly in the test region 90 and the control label 232 accumulates predominantly in the control region 92, although both the test label 230 and the control label 232 exhibit non-specific binding in the non-capture regions of the detection zone 15. The non-specific-binding compensation label 234, on the other hand, is distributed uniformly across the detection zone 15 due to the non-specific binding characteristics of the non-specific-binding compensation label.

In general, any of the implementations of the diagnostic test system that are described above may be used to obtain light intensity measurements from the various regions of the implementation of the test strip 50 that is shown in FIG. 12B. In some implementations, the data analyzer 46 (FIG. 3) compensates for the effects of non-specific binding on the measurements of the test and control labels 230, 232 in the test and control regions 90, 92 based on light intensity measurements obtained from the non-specific-binding compensation label 234.

Figure 13:
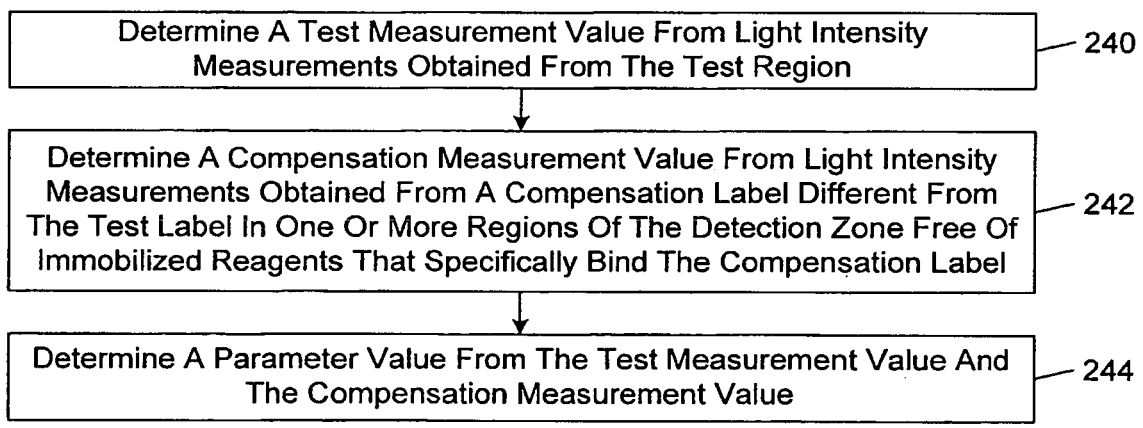
FIG. 13 is a flow diagram of an embodiment of a method executable by an embodiment of the data analyzer shown in FIG. 3.

FIG. 13 shows a flow diagram of an embodiment of a method by which the data analyzer 46 estimates the effects of non-specific binding on light intensity measurements that are obtained from a test label.

In accordance with this embodiment, the data analyzer 46 (FIG. 3) determines a test measurement value from light intensity measurements obtained from a test region containing an immobilized test reagent that specifically binds the target analyte (block 240). In some implementations, the test measurement value corresponds to a statistical measure (e.g., a peak intensity value or average intensity value) that is computed from the light intensity measurements that are obtained from the test region.

The data analyzer 46 also determines a compensation measurement value from light intensity measurements obtained from a compensation label in one or more regions of the detection zone 15 that are free of immobilized reagents that specifically bind the compensation label (block 242).

In general, the compensation label may be any label that is not specifically bound in the region from which the compensation measurement value is determined. For example, in some implementations, the compensation label may be the non-specific binding label 234. In other implementations, the compensation label may be the control label 232 when the compensation measurement is determined based on light intensity measurements obtained from a region (e.g., the test region) that is free of immobilized reagents that specifically bind the control label. In implementations in which the compensation label has a characteristic or property that is distinguishable from the test label and/or the control label (e.g., by different wavelengths of fluorescent emission), the compensation measurement may be determined from light intensity measurements obtained from the test and/or control regions. With respect to these implementations, the data analyzer 46 may determine respective compensation measurements from light intensity measurements obtained from within the regions of interest (e.g., the test and control regions) and from regions outside of the regions of interest. The data analyzer 46 may use these different compensation measurements in the determination of the evaluation parameter value.

The compensation measurement value may correspond to a statistical measure (e.g., a peak intensity value or average intensity value) that is computed from one or more regions of the detection zone that are free of immobilized reagents. In some implementations, the compensation measurement value is determined from light intensity measurements that are obtained from regions that are immediately adjacent to the test region. In other implementations, the compensation measurement value corresponds to an average light intensity value that is determined from light intensity measurements that are obtained from non-capture regions across the detection zone 15.

The data analyzer 46 (FIG. 3) determines a parameter value from the test measurement value and the compensation measurement value (block 244). The parameter value may be, for example, a relative quantity of the target analyte or an absolute quantity of the target analyte. A relative quantity of the target analyte may be determined by comparing (e.g., by difference or ratio operations) the test measurement value to the compensation measurement value.

An absolute quantity of the target analyte may be determined by correcting the test measurement value based on the compensation measurement value and comparing the corrected test measurement value to a calibration table that maps corrected test measurement values to target analyte quantities. The calibration table may be derived by the data analyzer 46 from light intensity measurements obtained from one or more calibration regions that may be included on the test strip.

In some implementations, the data analyzer 46 (FIG. 3) may determine an evaluation parameter value based on the determined test measurement value and the determined compensation measurement value. The evaluation parameter may correspond, for example, to a value (e.g., yes/no, or positive/negative) that indicates the result of an assay test. In some implementations, the data analyzer 46 compares the ratio of the test measurement value ($M_T$) and the compensation measurement value ($M_C$) to a threshold value (T1) to determine the evaluation parameter value (EP1). For example, If $(M_T)/(M_C)>T1$, EP1=1, otherwise, EP1=0.

In another implementation, the data analyzer 46 compares the difference between the test measurement value ($M_T$) and the compensation measurement value ($M_C$) to a threshold value (T2) to determine the evaluation parameter value (EP2). For example, If $(M_T)-(M_C)>T2$, EP2=1, otherwise, EP2=0.

In some embodiments, the data analyzer 46 (FIG. 3) may determine relative quantities of two different analytes (A, B) in a fluid sample based on test measurement values that are determined from light intensity measurements obtained from respective test regions with immobilized test reagents with respective binding affinities for the target analytes A, B. In these embodiments, the relative quantities ($MR_A$, $MR_B$) may correspond to test measurement values ($M_A$, $M_B$) that have been corrected by a determined compensation measurement value ($M_C$). For example, $MR_A = M_A - M_C$ $MR_B = M_B - M_C$ In some implementations, the data analyzer 46 (FIG. 3) compares the ratio of the corrected test measurement values ($M_A - M_C$, $M_B - M_C$) to a threshold value (T3) to determine an evaluation parameter value (EP3). For example, If $(M_A - M_C)/(M_B - M_C) > T3$, EP3=1, otherwise, EP3=0.

V. Conclusion

The embodiments that are described above provide lateral flow assay test strips that include multiple labels and systems and methods for reading such test strips that provide improved detection of different capture regions on the test strips, improved assay testing speed, and improved assay measurement sensitivity.

Other embodiments are within the scope of the claims.

What is claimed is:

1. An assay test strip, comprising:
   a flow path for a fluid sample;
   a sample receiving zone coupled to the flow path;
   at least one test label that specifically binds a target analyte;
   at least one control label that specifically binds an immobilized control reagent;
   at least one non-specific-binding label comprising a labeling substance and a probe substance that is free of any specific binding affinity for the target analyte and the immobilized control reagent, wherein the at least one non-specific-binding label is capable of compensating for effects of non-specific binding of the test label on light intensity measurements of the test label; and
   a detection zone coupled to the flow path downstream of the sample receiving zone and comprising at least one capture region including at least one immobilized reagent that specifically binds the target analyte and at least one immobilized reagent that specifically binds the at least one control label, wherein the detection zone is free of immobilized reagents that specifically bind the non-specific binding label, wherein the at least one test label, the at least one control label, and the at least one non-specific binding label are intermixed in the sample receiving zone.

2. The assay test strip of claim 1, wherein the at least one test label comprises at least one fluorescent particle of a first type which fluoresces at a first characteristic wavelength and the non-specific-binding label comprises at least one fluorescent particle of a second type which fluoresces at a second characteristic wavelength different from the first characteristic wavelength.

3. The assay test strip of claim 1, wherein the immobilized reagent that specifically binds the target analyte and the immobilized reagent that specifically binds the at least one control label are immobilized in a combined test-and-control region of the detection zone.

4. The assay test strip of claim 3, wherein the immobilized reagent that specifically binds the target analyte and the immobilized reagent that specifically binds the at least one control label are intermixed in the test-and-control region.

5. The assay test strip of claim 3, wherein the immobilized reagent that specifically binds the target analyte and the immobilized reagent that specifically binds the at least one control label are located in separate contiguous sub-regions of the test-and-control region.

6. The assay test strip of claim 3, wherein the combined test-and-control region has a plano-elliptical shape.

7. The assay test strip of claim 3, wherein the combined test-and-control region has a plano-circular shape.

8. The assay test strip of claim 1, wherein the test label comprises quantum dots of a first type and the non-specific binding label comprises quantum dots of a second type.

9. The assay test strip of claim 1, wherein the at least one test label comprises at least one reflective particle with reflective properties of a first type and the non-specific-binding label comprises at least one reflective particle with reflective properties of a second type.

10. The assay test strip of claim 1, wherein the at least one non-specific-binding label is capable of compensating for effects of non-specific binding of the control label on light intensity measurements of the control label.

* * * * *